(12) United States Patent
Kim et al.

(10) Patent No.: US 10,259,929 B2
(45) Date of Patent: Apr. 16, 2019

(54) RESIN COMPOSITION INCLUDING PLASTICIZER COMPOSITION, AND METHODS FOR PREPARING THE SAME

(71) Applicant: LG CHEM, LTD., Seoul (KR)

(72) Inventors: Hyun Kyu Kim, Daejeon (KR); Mi Yeon Lee, Daejeon (KR); Jeong Ju Moon, Daejeon (KR); Joo Ho Kim, Daejeon (KR); Seok Ho Jeong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 15/531,575

(22) PCT Filed: Apr. 6, 2016

(86) PCT No.: PCT/KR2016/003579
§ 371 (c)(1),
(2) Date: May 30, 2017

(87) PCT Pub. No.: WO2016/163742
PCT Pub. Date: Oct. 13, 2016

(65) Prior Publication Data
US 2018/0291179 A1    Oct. 11, 2018

(30) Foreign Application Priority Data

Apr. 6, 2015  (KR) .................. 10-2015-0048542
Apr. 6, 2015  (KR) .................. 10-2015-0048548
Mar. 31, 2016 (KR) .................. 10-2016-0039671

(51) Int. Cl.
*C08K 5/12*    (2006.01)
*C07C 69/80*   (2006.01)
*C08L 101/00*  (2006.01)
*C08J 3/20*    (2006.01)

(52) U.S. Cl.
CPC ............ *C08K 5/12* (2013.01); *C07C 69/80* (2013.01); *C08J 3/203* (2013.01); *C08L 101/00* (2013.01); *C08J 2327/06* (2013.01); *C08K 2201/014* (2013.01)

(58) Field of Classification Search
CPC ...... C08K 5/12; C08K 2201/014; C08J 3/203; C08J 2327/06
USPC ....................................... 524/114
See application file for complete search history.

(56) References Cited

U.S. PATENT DOCUMENTS

| | | | |
|---|---|---|---|
| 3,355,471 A * | 11/1967 | Kebrich | C07C 63/24 524/396 |
| 3,440,213 A | 4/1969 | Kebrich et al. | |
| 5,262,444 A * | 11/1993 | Rusincovitch | B32B 27/22 521/50.5 |
| 5,319,025 A | 6/1994 | Nakamura et al. | |
| 2002/0188077 A1 | 12/2002 | Kumaki et al. | |
| 2004/0027520 A1 | 2/2004 | Elman et al. | |
| 2004/0138386 A1 | 7/2004 | Kumaki et al. | |
| 2005/0256288 A1 | 11/2005 | Zhu et al. | |
| 2007/0037926 A1 | 2/2007 | Olsen et al. | |
| 2011/0021680 A1 | 1/2011 | Colle et al. | |
| 2013/0137789 A1 | 5/2013 | Olsen et al. | |
| 2014/0228494 A1 | 8/2014 | Colle et al. | |
| 2017/0166724 A1 | 6/2017 | Kim et al. | |

FOREIGN PATENT DOCUMENTS

| | | | |
|---|---|---|---|
| CN | 1419586 A | 5/2003 | |
| CN | 1487343 A | 4/2004 | |
| CN | 1696189 A | 11/2005 | |
| CN | 1968981 A | 5/2007 | |
| CN | 101238175 A | 8/2008 | |
| CN | 101981106 B | 12/2012 | |
| CN | 102995451 A | 3/2013 | |
| CN | 103131145 A | 6/2013 | |
| CN | 103820042 A | 5/2014 | |
| CN | 104327513 A | 2/2015 | |
| EP | 3103788 A1 | 12/2016 | |
| GB | 851753 A | 10/1960 | |
| GB | 851753 A * | 10/1960 | ............... C08K 5/12 |
| GB | 1021388 A | 3/1966 | |
| GB | 1021388 A * | 3/1966 | ............ C08F 259/04 |
| JP | 61243845 A | 10/1986 | |
| JP | 2012089287 A | 5/2012 | |
| KR | 101458311 B1 | 11/2014 | |

OTHER PUBLICATIONS

Database WPI, 2017 Clarivate Analytics, Week 201454, Thomas Scientific, London, GB; AN 2014-N74280, XP002778077 (related to CN 103820042 A, published May 28, 2014).
Database WPI, 2017 Clarivate Analytics, Week 201529, Thomas Scientific, London, GB; AN 2015-20260C, XP002778078 (related to CN 104327513 A, published Feb. 4, 2015).
Database WPI, 2017 Clarivate Analytics, Week 198650, Thomas Scientific, London, GB; AN 1986-328423, XP002778127 (related to JP S61-243845 A, published Oct. 30, 1986).

* cited by examiner

*Primary Examiner* — Hui H Chin
(74) *Attorney, Agent, or Firm* — Dentons US LLP

(57) ABSTRACT

The present invention relates to a plasticizer composition, a resin composition and methods for preparing the plasticizer composition and the resin composition, and provides a plasticizer composition capable of improving physical properties such as plasticizing efficiency, tensile and elongation retention, volatile loss and migration resistance, which are required for a plasticizer composition included in a vinyl chloride-based resin composition, to an equal or a higher level compared to existing plasticizer compositions, and a resin composition including the same.

12 Claims, No Drawings

US 10,259,929 B2

RESIN COMPOSITION INCLUDING PLASTICIZER COMPOSITION, AND METHODS FOR PREPARING THE SAME

CROSS-REFERENCE(S) TO RELATED APPLICATION

This application is a National Stage Entry of International Application No. PCT/KR2016/003579, filed on Apr. 6, 2016, and claims the benefit of and priority to Korean Application No. 10-2015-0048542, filed on Apr. 6, 2015, Korean Application No. 10-2015-0048548, filed on Apr. 6, 2015, and Korean Application No. 10-2016-0039671, filed on Mar. 31, 2016 all of which are hereby incorporated by reference in their entirety for all purposes as if fully set forth herein.

FIELD OF THE INVENTION

The present invention relates to a resin composition, a plasticizer composition included therein, and a method for preparing the resin composition.

DESCRIPTION OF THE RELATED ART

In common plasticizers, alcohols react with polycarboxylic acids such as phthalic acid and adipic acid to form esters corresponding thereto. In addition, studies on plasticizer compositions capable of replacing phthalate-based plasticizers such as terephthalate-based, adipate-based and other polymer-based have been continued considering domestic and overseas restrictions on phthalate-based plasticizers harmful to the human body.

Meanwhile, proper plasticizers need to be used considering not only high heat resistance and low volatile loss, main required physical properties in compound industries, but also a migration property, volatile loss, plasticizing efficiency and the like, required physical properties in industries of flooring materials, sheets for water play and films and the like. In PCV compounds used for flooring materials, films, calendaring sheets, wires or cables, additives such as a plasticizer, a stabilizer and a pigment are mixed to a PVC resin depending on tensile strength, an elongation rate, plasticizing efficiency, volatile loss, a migration property, tensile and elongation retention and the like, required properties in the corresponding standard.

Several phthalate products represented as dioctyl phthalate among plasticizer products are currently under environmental restrictions in various product groups due to their harmfulness to the human body, and such a trend has expanded development and use of environmental-friendly plasticizers, and cyclically, environmental-friendly plasticizer market domains are expanded in more diverse products and industries. In order to meet such a market trend, development of new environmental-friendly products with equal or higher qualities capable of replacing phthalate has been required.

However, despite such environmental restrictions, products such as di-2-propylheptyl phthalate are not subject to environmental restrictions, and diversely used in industrial fields. Accordingly, in order to develop optimal products considering both quality aspects and price aspects together with the development of such new environmental-friendly products, studies for securing vinyl chloride-based resin compositions capable of being used have been progressed focusing on products and industries without restrictions.

DISCLOSURE OF THE INVENTION

Technical Problem

In view of the above, while continuously performing researches on plasticizers, the inventors of the present invention have identified a plasticizer composition capable of improving physical properties of a vinyl chloride-based resin composition, and completed the present invention.

In other words, an object of the present invention is to provide a plasticizer composition capable of improving physical properties such as hardness, tensile and elongation retention, migration resistance and volatile loss when used as a plasticizer of a resin composition, a method for preparing the same, and a resin composition including the same.

Technical Solution

One embodiment of the present invention provides a resin composition including 100 parts by weight of a resin; 1 part by weight to 80 parts by weight of a plasticizer composition, wherein the plasticizer composition includes an isophthalate-based material and a phthalate-based material, and the isophthalate-based material and the phthalate-based material have a weight ratio of 99:1 to 1:99.

The isophthalate-based material may include diisononyl isophthalate (DINIP), diethylhexyl isophthalate (DEHIP or DOIP) or a mixture thereof.

The isophthalate-based material and the phthalate-based material may have a weight ratio of 99:1 to 20:80.

The isophthalate-based material and the phthalate-based material may have a weight ratio of 99:1 to 40:60.

The isophthalate-based material and the phthalate-based material may have a weight ratio of 99:1 to 30:70.

The isophthalate-based material and the phthalate-based material may have a weight ratio of 99:1 to 70:30.

The phthalate-based material may include one or more selected from the group consisting of diisodecyl phthalate (DIDP) and di(2-propylheptyl)phthalate (DPHP).

The plasticizer composition may further include an additive, and the additive may be included in 1 part by weight to 100 parts by weight with respect to 100 parts by weight of a mixed weight of the isophthalate-based material and the phthalate-based material.

The additive may include any one selected from the group consisting of citrate-based compounds, trimellitate-based compounds and epoxidized fatty acid alkyl ester compounds.

The additive may include one or more types selected from the group consisting of epoxy fatty acid methyl ester (eFAME), acetyl tributyl citrate (ATBC), tributyl citrate (TBC), acetyl triethylhexyl citrate (ATEHC), triethylhexyl citrate (TEHC), acetyl triisononyl citrate (ATINC), triisononyl citrate (TINC), triisobutyl trimetllitate (TiBTM), trinormalbutyl trimetllitate (TnBTM), triethylhexyl trimetllitate (TEHTM) and triisononyl trimetllitate (TINTM).

The resin may be one or more types selected from the group consisting of ethylene vinyl acetate, polyethylene, polyketone, polypropylene, polyvinyl chloride, polystyrene, polyurethane and thermoplastic elastomers.

The resin composition may be used in manufacturing one or more types selected from the group consisting of wires, flooring materials, automotive interior materials, films, sheets, wallpapers and tubes.

Another embodiment of the present invention provides a method for preparing a plasticizer composition including preparing an isophthalate-based material and a phthalate-based material; and obtaining a plasticizer composition by blending the isophthalate-based material and the phthalate-based material to have a weight ratio of 99:1 to 1:99.

After the obtaining of a plasticizer composition through blending, the method may further include mixing an additive in 1 part by weight to 100 parts by weight with respect to 100 parts by weight of a mixed weight of the isophthalate-based material and the phthalate-based material.

The additive may include one or more compounds selected from the group consisting of citrate-based compounds, trimellitate-based compounds and epoxidized fatty acid alkyl ester compounds.

Advantageous Effects

A plasticizer composition according to one embodiment of the present invention is capable of providing excellent properties in migration resistance and volatile loss and the like as well as enhancing properties such as plasticizing efficiency, tensile strength and an elongation rate when used in a resin composition.

MODE FOR CARRYING OUT THE INVENTION

Example

Hereinafter, the present invention will be described in detail with reference to examples. However, the examples according to the present invention may be modified to various other forms, and the scope of the present invention should not be construed as being limited to the examples described below. The examples of the present invention are provided in order to more completely describe the present invention for those having average knowledge in the art.

Preparation Example 1

Preparation of Diisononyl Isophthalate (DINIP)

To a 4-neck 3 liter reactor provided with a cooler, a water stripper, a condenser, a decanter, a reflux pump, a temperature controller, a stirrer and the like, 498.0 g of purified isophthalic acid (PIA), 1298.3 g of isononyl alcohol (INA) (molar ratio of PIA:INA was 1.0:3.0), and 1.54 g of a titanium-based catalyst (TIPT, tetra isopropyl titanate) as a catalyst (0.31 parts by weight with respect to 100 parts by weight of the PIA) were introduced, and the temperature was slowly raised up to approximately 170° C. Produced water started to be generated near approximately 170° C., and an ester reaction was carried out for approximately 4.5 hours while continuously introducing nitrogen gas at a reaction temperature of approximately 220° C. and under atmospheric pressure, and the reaction was completed when an acid value reached 0.01.

After the reaction was complete, distillation extraction was carried out for 0.5 hours to 4 hours under reduced pressure in order to remove unreacted raw materials. Steam distillation was carried out for 0.5 hours to 3 hours under reduced pressure using steam in order to remove unreacted raw materials to a specific content level or lower, and neutralization treatment was carried out using an alkali solution after cooling the reaction solution to approximately 90° C. Water flushing may be additionally carried out and then moisture was removed through dehydrating the reaction solution. A filter medium was introduced to the moisture-removed reaction solution, and result was stirred for a certain period of time and then filtered to finally obtain 1243.3 g of diisononyl isophthalate (yield: 99.0%).

Preparation Example 2

Preparation of Diethylhexyl Isophthalate (DOIP)

Preparation was carried out in the same manner as in Preparation Example 1 except that ethylhexyl alcohol was used instead of isononyl alcohol, and 1148.1 g of diethylhexyl isophthalate (yield: 98%) was finally obtained.

Preparation Example 3

Preparation of DPHP 444 g of phthalic acid and 1240 g of propylheptyl alcohol were used as reaction materials to finally obtain 1320 g of dipropylheptyl phthalate (DPHP) (yield: 98%).

Preparation Example 4

Preparation of DIDP 444 g of phthalic acid and 1235 g of isodecyl alcohol were used as reaction materials to finally obtain 1313 g of diisodecyl phthalate (DIDP) (yield: 98%).

Plasticizer compositions of Examples 1 to 4 were prepared using the materials prepared in the preparation examples, and the preparations are summarized in the following Tables 1 and 2. Physical property evaluations on the plasticizer compositions were carried out according to the following test items.

TABLE 1

| | Isophthalate-based Material | Phthalate-based Material | Mixing Weight Ratio |
|---|---|---|---|
| Example 1-1 | Preparation Example 1 (DINIP) | Preparation Example 3 (DPHP) | 9:1 |
| Example 1-2 | | | 7:3 |
| Example 1-3 | | | 5:5 |
| Example 1-4 | | | 3:7 |
| Example 1-5 | | | 1:9 |
| Example 2-1 | | Preparation Example 4 (DIDP) | 9:1 |
| Example 2-2 | | | 7:3 |
| Example 2-3 | | | 5:5 |
| Example 2-4 | | | 3:7 |
| Example 2-5 | | | 1:9 |

TABLE 2

| | Isophthalate-based Material | Phthalate-based Material | Mixing Weight Ratio |
|---|---|---|---|
| Example 3-1 | Preparation Example 2 (DOIP) | Preparation Example 3 (DPHP) | 9:1 |
| Example 3-2 | | | 7:3 |
| Example 3-3 | | | 5:5 |
| Example 3-4 | | | 1:9 |
| Example 4-1 | | Preparation Example 4 (DIDP) | 9:1 |
| Example 4-2 | | | 7:3 |
| Example 4-3 | | | 5:5 |
| Example 4-4 | | | 1:9 |

<Test Items>

Measurement conditions for the following test items may be for illustrative purposes for describing measurement methods, and specific measurement and evaluation conditions for the test examples using other conditions may be referred to in each of the test examples.

Measurement on Hardness

Shore hardness at 25° C., 3T 10 s, was measured in accordance with the ASTM D2240.

Measurement on Tensile Strength

After pulling a cross head speed at 200 mm/min (1T) using U.T.M (manufacturer; Instron, model name; 4466), a test device, in accordance with the ASTM D638 method, the spot at which the specimen was cut was measured. Tensile strength was calculated as follows:

Tensile strength (kgf/mm$^2$)=load value (kgf)/thickness (mm)×width (mm)

Measurement on Elongation Rate

After pulling a cross head speed at 200 mm/min (1T) using the U.T.M in accordance with the ASTM D638 method, the spot at which the specimen was cut was measured, and then an elongation rate was calculated as follows:

Elongation rate (%)=[length after elongation/initial length]×100.

Measurement on Tensile and Elongation Retention

Measurement on tensile and elongation retention measures tensile and elongation rate properties remaining on the specimen after applying heat for a certain period of time at a specific temperature, and the methods of measurement are the same as the methods measuring the tensile strength and the elongation rate.

Measurement on Migration Loss

A specimen having a thickness of 2 mm or greater was obtained in accordance with the KSM-3156, and a load of 1 kgf/cm$^2$ was applied after attaching PS plates on both surfaces of the specimen. The specimen was left unattended for 72 hours in a forced convection oven (80° C.) and then taken out and cooled for 4 hours at room temperature. After that, the PS plates attached on both surfaces of the specimen were removed, weights before and after leaving the specimen unattended in the oven were measured, and the amount of migration loss was calculated through the equation such as below.

Amount of migration loss (%)=[(initial weight of specimen at room temperature−weight of specimen after being left unattended in oven)/initial weight of specimen at room temperature]×100

Measurement on Volatile Loss

After working on the prepared specimen for 72 hours at 80° C., the weight of the specimen was measured.

Volatile loss (%)=[(initial specimen weight−specimen weight after working)/initial specimen weight]×100.

Measurement on Absorption Rate

An absorption rate was evaluated such that the resin and the ester compound were mixed to each other under a condition of 77 and 60 rpm using a Planatary mixer (Brabender, P600), and the time taken for the torque of the mixer to be stabilized was measured.

Stress Test

As for the stress test, the specimen was left unattended for a certain period of time as being bent, and the degree of migration (the degree of ooze) was observed and expressed as a number. The number being closer to 0 represents excellent properties.

Measurement on Cold Resistance 5 prepared specimens were left unattended for 3 minutes at a specific temperature and then were hit, and a temperature at which 3 out of the 5 specimens were destroyed was measured.

Test Example 1

Mixed Plasticizer Composition of DINIP and DPHP

Mixed plasticizer compositions were obtained by mixing DINIP and DPHP in the mixing ratios of Examples 1-1 to 1-5 listed in Table 1, and these were used as specimens for the tests, and as Comparative Examples 1 to 3, single plasticizer compositions of DINIP, DPHP and DIDP, respectively, were used.

As for the preparation of the specimens, 50 parts by weight of the plasticizer composition prepared in the examples and the comparative examples, 3 parts by weight of RUP-144 (Adeka Korea Corporation) as a stabilizer, 40 parts by weight of Omya 1T (Omya Group) as a filler and 0.3 parts by weight of St-A (ISU Chemical) as a lubricant were mixed with respect to 100 parts by weight of a polyvinyl chloride resin (PVC (LS100)) under 98° C. and 700 rpm referring to the ASTM D638. The specimens were prepared by working on the result for 4 minutes at 160° C. using a roll mill, and then working on the result for 2.5 minutes (low pressure) and 2 minutes (high pressure) at 180° C. using a press.

For the specimens, the test items were each evaluated, and the results are shown in the following Table 3.

TABLE 3

| | Plasticizer | Hardness (Shore "A") | Tensile Strength (kg/cm$^2$) | Tensile Retention (%) | Elongation Rate (%) | Elongation Retention (%) | Migration Loss (%) | Volatile Loss (%) | Cold Resistance (° C.) | Stress (168 hr) |
|---|---|---|---|---|---|---|---|---|---|---|
| Example 1-1 | 9:1 | 86.3 | 198.0 | 98.9 | 317.6 | 95.0 | 1.37 | 1.29 | −30 | 2.5 |
| Example 1-2 | 7:3 | 86.5 | 190.5 | 98.8 | 314.6 | 96.9 | 1.15 | 1.27 | −31 | 1.0 |
| Example 1-3 | 5:5 | 86.5 | 187.4 | 97.8 | 313.8 | 96.8 | 1.13 | 1.55 | −29 | 0.5 |
| Example 1-4 | 3:7 | 87.1 | 184.4 | 95.1 | 310.1 | 88.1 | 1.07 | 1.60 | −29 | 0.5 |
| Example 1-5 | 1:9 | 87.5 | 181.9 | 90.5 | 306.1 | 86.4 | 1.05 | 1.85 | −29 | 0.5 |
| Comparative Example 1 | DINIP | 86.2 | 198.3 | 99.1 | 319.3 | 93.2 | 1.77 | 1.23 | −30 | 2.5 |

TABLE 3-continued

| | Plasticizer | Hardness (Shore "A") | Tensile Strength (kg/cm$^2$) | Tensile Retention (%) | Elongation Rate (%) | Elongation Retention (%) | Migration Loss (%) | Volatile Loss (%) | Cold Resistance (° C.) | Stress (168 hr) |
|---|---|---|---|---|---|---|---|---|---|---|
| Comparative Example 2 | DPHP | 88.3 | 173.4 | 90.1 | 298.1 | 84.3 | 1.01 | 2.56 | −29 | 0.5 |

Hardness: 3T, 10 s
Tensile strength and elongation rate: 1T, 200 mm/min
Tensile retention and elongation retention: 121° C., 168 hr
Migration loss: 80° C., 1T, 1 kgf/cm$^2$, 72 hr
Volatile loss: 100° C., 72 hr
Absorption rate: 88° C.
Stress test: 23° C., 168 hr As shown in Table 3, it was seen that, when comparing the compounds of Comparative Examples 1 and 2 using a single plasticizer composition and the compounds of Examples 1-1 to 1-5, the compounds of Examples 1-1 to 1-5 exhibited similar, or equal or better physical properties compared to the compound of Comparative Example 1 or 2. It was identified that, in Comparative Examples 1 and 2, controlling the physical properties of the compounds was difficult since, in tensile strength or tensile and elongation retention, and migration loss and volatile loss, the properties were weighed to either of them, but when DPHP, a phthalate material, was mixed to DINIP in a proper amount, physical properties were properly controlled depending on the adjustment of the amount, and superior values were able to be secured.

Through the results described above, it was identified that an effect of improving a migration property and stress migration may be obtained through efficiently mixing DINIP with a phthalate-based material such as DPHP even with the DINIP having poor migration property and stress migration despite excellent plasticizing efficiency, tensile strength, tensile retention, an elongation rate, elongation retention and volatile loss. In other words, it was identified that the resin composition using a plasticizer composition mixing an isophthalate-based material and a phthalate-based material may prepare compounds capable of providing more superior physical properties compared to the resin composition using a single plasticizer composition.

Concomitantly, it was identified that mixing a phthalate material with DINIP that does not have price competitiveness despite excellent physical properties did not experience physical property decline, and consequently, it was also identified that price competitiveness of a plasticizer composition using DINIP was capable of being secured therethrough.

Test Example 2

Mixed Plasticizer Composition of DINIP and DIDP

Mixed plasticizer compositions were obtained by mixing DINIP and DIDP in the mixing ratios of Examples 2-1 to 2-5 listed in Table 1, and these were used as specimens for the tests.

As for the preparation of the specimens, 50 parts by weight of the plasticizer composition prepared in the examples and the comparative examples, 5 parts by weight of RUP-144 (Adeka Korea Corporation) as a stabilizer, 40 parts by weight of Omya 1T (Omya Group) as a filler and 0.3 parts by weight of St-A (ISU Chemical) as a lubricant were mixed with respect to 100 parts by weight of a polyvinyl chloride resin (PVC (LS100)) under 98° C. and 700 rpm referring to the ASTM D638. The specimens were prepared by working on the result for 4 minutes at 160° C. using a roll mill, and then working on the result for 2.5 minutes (low pressure) and 2 minutes (high pressure) at 180° C. using a press.

For the specimens, the test items were each evaluated (in the retention evaluation, the temperature was 121° C. instead of 100° C.), and the results are shown in the following Tables 4 and 5.

TABLE 4

| | Plasticizer | Hardness (Shore "A") | Tensile Strength (kg/cm$^2$) | Tensile Retention (%) | Elongation Rate (%) | Elongation Retention (%) | Migration Loss (%) | Volatile Loss (%) |
|---|---|---|---|---|---|---|---|---|
| Example 2-1 | 9:1 | 90.6 | 189.09 | 95 | 299.48 | 99 | 1.26 | 1.20 |
| Example 2-2 | 7:3 | 90.5 | 188.18 | 97 | 290.85 | 99 | 1.22 | 1.19 |
| Example 2-3 | 5:5 | 90.5 | 186.37 | 97 | 288.05 | 95 | 1.03 | 1.23 |
| Example 2-4 | 3:7 | 90.3 | 185.06 | 97 | 284.94 | 94 | 1.08 | 1.27 |
| Example 2-5 | 1:9 | 90.3 | 178.23 | 95 | 282.42 | 88 | 0.87 | 1.28 |
| Comparative Example 1 | DINIP | 90.5 | 181.95 | 95 | 296.24 | 99 | 1.69 | 1.08 |

TABLE 4-continued

| | Plasticizer | Hardness (Shore "A") | Tensile Strength (kg/cm$^2$) | Tensile Retention (%) | Elongation Rate (%) | Elongation Retention (%) | Migration Loss (%) | Volatile Loss (%) |
|---|---|---|---|---|---|---|---|---|
| Comparative Example 3 | DIDP | 90.5 | 163.55 | 97 | 270.37 | 86 | 0.74 | 1.40 |

Hardness: 3T, 10 s
Tensile strength and elongation rate: 1T, 200 mm/min
Tensile retention and elongation retention: 121° C., 168 hr
Migration loss: 80° C., 1T, 1 kgf/cm$^2$, 72 hr
Volatile loss: 100° C., 72 hr
Absorption rate: 88° C.
Stress test: 23° C., 168 hr

TABLE 5

| | Plasticizer | 24 hr | 72 hr | 168 hr |
|---|---|---|---|---|
| Example 2-1 | 9:1 | 1 | 2 | 2 |
| Example 2-2 | 7:3 | 0.5 | 1.5 | 1 |
| Example 2-3 | 5:5 | 0.5 | 0.5 | 0 |
| Example 2-4 | 3:7 | 0 | 0 | 0 |
| Example 2-5 | 1:9 | 0 | 0 | 0 |
| Comparative Example 1 | DINIP | 1.5 | 2 | 2 |
| Comparative Example 3 | DIDP | 0 | 0 | 0 |

As shown in Tables 4 and 5, it was seen that, when comparing the compounds of Comparative Examples 1 and 3 using a single plasticizer composition and the compounds of Examples 2-1 to 2-5, the compounds of Examples 2-1 to 2-5 exhibited similar, or equal or better physical properties compared to the compound of Comparative Example 1 or 3. It was identified that, in Comparative Examples 1 and 3, controlling the physical properties of the compounds was difficult since, particularly in stress migration as well as tensile strength or an elongation rate, or elongation retention, and migration loss and volatile loss, the properties were weighed to either of them, but when DIDP, a phthalate material, was mixed to DINIP in a proper amount, physical properties were properly controlled depending on the adjustment of the amount, and superior values were able to be secured.

In other words, it was identified that the resin composition using a plasticizer composition mixing DINIP and a phthalate-based material of the present invention may prepare compounds capable of providing more superior physical properties compared to the resin composition using a single plasticizer composition.

Moreover, it was identified that mixing a phthalate material with DINIP that does not have price competitiveness despite excellent physical properties did not experience physical property decline, and consequently, it was also identified that price competitiveness of a plasticizer composition using DINIP was capable of being secured therethrough.

Test Example 3

Mixed Plasticizer Composition of DOIP and DPHP

Mixed plasticizer compositions were obtained by mixing DOIP and DPHP in the mixing ratios of Examples 3-1 to 3-4 listed in Table 2, and these were used as specimens for the tests, and as Comparative Example 4, a single plasticizer composition of DIOP was used As for the preparation of the specimens, 50 parts by weight of the plasticizer composition prepared in the examples and the comparative examples, 3 parts by weight of RUP-144 (Adeka Korea Corporation) as a stabilizer and 40 parts by weight of Omya 1T (Omya Group) as a filler were mixed with respect to 100 parts by weight of a polyvinyl chloride resin (PVC (LS100)) under 98° C. and 700 rpm referring to the ASTM D638. The specimens were prepared by working on the result for 4 minutes at 160° C. using a roll mill, and then working on the result for 2.5 minutes (low pressure) and 2 minutes (high pressure) at 180° C. using a press.

For the specimens, the test items were each evaluated, and the results are shown in the following Table 6.

TABLE 6

| | Plasticizer | Hardness (Shore "A") | Tensile Strength (kg/cm$^2$) | Tensile Retention (%) | Elongation Rate (%) | Elongation Retention (%) | Migration Loss (%) | Volatile Loss (%) | Cold Resistance (° C.) | Stress (168 hr) |
|---|---|---|---|---|---|---|---|---|---|---|
| Example 3-1 | 9:1 | 84.1 | 187.4 | 101.6 | 326.0 | 96.3 | 2.20 | 1.56 | −28 | 1.5 |
| Example 3-2 | 7:3 | 85.0 | 186.6 | 100.1 | 324.7 | 95.2 | 2.01 | 0.85 | −27 | 0.5 |
| Example 3-3 | 5:5 | 85.8 | 183.5 | 101.7 | 325.6 | 94.0 | 1.85 | 0.43 | −27 | 0 |
| Example 3-4 | 1:9 | 86.8 | 176.3 | 98.2 | 315.3 | 90.9 | 1.66 | 0.40 | −27 | 0 |
| Comparative Example 4 | DOIP | 84.2 | 191.6 | 102.8 | 337.0 | 97.1 | 3.78 | 2.31 | −28 | 3 |

TABLE 6-continued

| | Plasticizer | Hardness (Shore "A") | Tensile Strength (kg/cm$^2$) | Tensile Retention (%) | Elongation Rate (%) | Elongation Retention (%) | Migration Loss (%) | Volatile Loss (%) | Cold Resistance (° C.) | Stress (168 hr) |
|---|---|---|---|---|---|---|---|---|---|---|
| Comparative Example 2 | DPHP | 88.3 | 170.9 | 93.2 | 308.7 | 84.2 | 1.55 | 0.35 | −27 | 0 |

Hardness: 3T, 10 s
Tensile strength and elongation rate: 1T, 200 mm/min
Tensile retention and elongation retention: 100° C., 168 hr
Migration loss: 80° C., 1T, 2 kgf/cm$^2$, 72 hr
Volatile loss: 100° C., 168 hr
Stress test: 23° C., 168 hr As shown in Table 6, it was identified that, when comparing the compounds of Comparative Examples 2 and 4 using a single plasticizer composition and the compounds of Examples 3-1 to 3-4, the compounds of Examples 3-1 to 3-4 exhibited similar, or equal or better physical properties compared to the compounds of the comparative examples. It was identified that, in Comparative Examples 2 and 4, controlling the physical properties of the compounds was difficult since, particularly in stress migration as well as tensile strength or an elongation rate, or elongation retention, and migration loss and volatile loss, the properties were weighed to either of them, but when DPHP, a phthalate material, was mixed to DOIP in a proper amount, physical properties were properly controlled depending on the adjustment of the amount, and superior values were able to be secured.

As for the preparation of the specimens, 50 parts by weight of the plasticizer composition prepared in the examples and the comparative examples, 5 parts by weight of RUP-144 (Adeka Korea Corporation) as a stabilizer and 40 parts by weight of Omya 1T (Omya Group) as a filler were mixed with respect to 100 parts by weight of a polyvinyl chloride resin (PVC (LS100)) under 98° C. and 700 rpm referring to the ASTM D638. The specimens were prepared by working on the result for 4 minutes at 160° C. using a roll mill, and then working on the result for 2.5 minutes (low pressure) and 2 minutes (high pressure) at 180° C. using a press.

For the specimens, the test items were each evaluated, and the results are shown in the following Table 7.

TABLE 7

| | Plasticizer | Hardness (Shore "A") | Tensile Strength (kg/cm$^2$) | Tensile Retention (%) | Elongation Rate (%) | Elongation Retention (%) | Migration Loss (%) | Volatile Loss (%) | Cold Resistance (° C.) | Stress (168 hr) |
|---|---|---|---|---|---|---|---|---|---|---|
| Example 4-1 | 9:1 | 84.8 | 189.5 | 98.4 | 328.1 | 96.3 | 2.74 | 3.33 | −29 | 2.0 |
| Example 4-2 | 7:3 | 85.2 | 188.9 | 99.8 | 322.5 | 95.9 | 1.88 | 1.26 | −29 | 1.0 |
| Example 4-3 | 5:5 | 86.0 | 186.9 | 96.4 | 317.9 | 95.3 | 1.56 | 0.85 | −29.5 | 0.5 |
| Example 4-4 | 1:9 | 86.4 | 179.1 | 94.1 | 310.3 | 94.6 | 1.33 | 0.71 | −29 | 0.5 |
| Comparative Example 4 | DOIP | 84.5 | 189.4 | 99.9 | 333.7 | 96.7 | 3.88 | 3.68 | −28 | 2.0 |
| Comparative Example 3 | DIDP | 87.3 | 175.5 | 92.2 | 300.8 | 94.2 | 1.19 | 0.85 | −30 | 1.0 |

Hardness 3T, 10 s
Tensile strength and elongation rate: 1T, 200 mm/min
Tensile retention and elongation retention: 100° C., 168 hr
Migration loss: 80° C., 1T, 2 kgf/cm$^2$, 72 hr
Volatile loss: 100° C., 168 hr
Stress test: 23° C., 168 hr In other words, it was identified that the resin composition using a plasticizer composition mixing DOIP and a phthalate-based material of the present invention may prepare compounds capable of providing more superior physical properties compared to the resin composition using a single plasticizer composition.

Test Example 4

Mixed Plasticizer Composition of DOIP and DIDP

Mixed plasticizer compositions were obtained by mixing DOIP and DIDP in the mixing ratios of Examples 4-1 to 4-4 listed in Table 2, and these were used as specimens for the tests.

As shown in Table 7, it was identified that, when comparing the compounds of Comparative Examples 3 and 4 using a single plasticizer composition and the compounds of Examples 4-1 to 4-4, the compounds of Examples 4-1 to 4-4 exhibited similar, or equal or better physical properties compared to the compounds of the comparative examples. It was identified that, in Comparative Examples 3 and 4, controlling the physical properties of the compounds was difficult since, particularly in stress migration as well as tensile strength or an elongation rate, or elongation retention, and migration loss and volatile loss, the properties were weighed to either of them, but when DIDP, a phthalate material, was mixed to DOIP in a proper amount, physical properties were properly controlled depending on the adjustment of the amount, and superior values were able to be secured.

In other words, it was identified that the resin composition using a plasticizer composition mixing DOIP and a phthalate-based material of the present invention may prepare compounds capable of providing more superior physical properties compared to the resin composition using a single plasticizer composition.

Hereinbefore, preferred examples of the present invention has been described in detail, however, the scope of the present invention is not limited thereto, and various modifications and improvements of those skilled in the art using the basic concept of the present invention defined in the claims are also included in the scope of the present invention.

Hereinafter, the present invention will be described in detail.

One embodiment of the present invention provides a resin composition including 100 parts by weight of a resin; 1 part by weight to 80 parts by weight of a plasticizer composition, wherein the plasticizer composition includes an isophthalate-based material and a phthalate-based material, and the isophthalate-based material and the phthalate-based material have a weight ratio of 99:1 to 1:99.

When the plasticizer composition is included in the resin composition in greater than 80 parts by weight, content of the plasticizer introduced for securing flexibility of the resin is too high, which may affect physical properties of the resin itself, and an effect of improving physical properties of the resin obtained through the plasticizer may not be high when the amount of the plasticizer exceeds a certain amount, which may cause economic loss. Accordingly, the plasticizer composition may be added in 1 part by weight to 80 parts by weight and preferably in 5 parts by weight to 70 parts by weight with respect to 100 parts by weight of the resin.

The isophthalate-based material may be used in content selected from a range of 1% by weight to 99% by weight, 10% by weight to 99% by weight, 20% by weight to 99% by weight, 30% by weight to 95% by weight, 40% by weight to 90% by weight or the like based on the total weight of the composition. In addition, the content may also be selected from a range of 1% by weight to 50% by weight, 10% by weight to 50% by weight, 10% by weight to 40% by weight, 25% by weight to 50% by weight, 25% by weight to 40% by weight or the like.

The isophthalate-based material may be diisononyl isophthalate (DINIP), diethylhexyl isophthalate (DEHIP or DOIP) or a mixture thereof. Diisononyl isophthalate may be preferably used, but the material is not limited thereto, and when being mixed with other compounds, the use may vary depending on an added amount.

The plasticizer composition includes an isophthalate-based material, and further includes a phthalate-based material. As above, the resin prepared with a plasticizer composition in which the isophthalate-based material and the phthalate-based material are mixed together may have more superior physical properties such as tensile strength or an elongation rate, and may have excellent volatile loss and migration resistance compared to a resin prepared with a plasticizer composition including the isophthalate-based material alone.

Herein, the isophthalate-based material and the phthalate-based material may be included in the plasticizer composition in a weight ratio of 99:1 to 1:99.

When the isophthalate-based material is diisononyl isophthalate, mixing with the phthalate-based material is more unrestricted, and for example, the ratio may be 99:1 to 1:99, 99:1 to 10:90, 99:1 to 20:80, or 99:1 to 30:70, and may be 99:1 to 40:60. Preferably, a ratio of 99:1 to 60:40 or 99:1 to 70:30 may be used. In such ranges, physical properties such as tensile strength or an elongation rate may be excellent.

Examples of the phthalate-based material may include diisodecyl phthalate (DIDP), di(2-propylheptyl)phthalate (DPHP) or a mixture thereof.

However, di(2-propylheptyl)phthalate may be preferably used as the phthalate-based material, and the di(2-propylheptyl)phthalate has a potential to be more advantageously used in many ways, and the di(2-propylheptyl) phthalate being relatively environmental friendly compared to other phthalate-based materials may be considered as an advantage.

The plasticizer composition may further include an additive, and the additive may be included in 1 part by weight to 100 parts by weight and preferably in 1 part by weight to 80 parts by weight with respect to 100 parts by weight of a mixed weight of the isophthalate-based material and the phthalate-based material. The additive may be included with the isophthalate-based material alone to enhance physical properties such as a stress property of a resin composition, however, even when such a small amount of the additive is included in the mixed plasticizer composition, compounds and the like having excellent physical properties may be prepared. When a larger quantity of the additive is included, physical properties of the plasticizer composition may be out of control in controlling physical properties suitable for application, and problems such as excessively improving undesirable physical properties or declining desirable physical properties may occur.

The additive may include any one selected from the group consisting of citrate-based compounds, trimellitate-based compounds and epoxidized fatty acid alkyl ester compounds.

Epoxy fatty acid methyl ester (eFAME) is most common as the epoxidized fatty acid alkyl ester, and the citrate-based compound may use various citrate-based compounds. Examples thereof may include acetyl tributyl citrate (ATBC), tributyl citrate (TBC), acetyl triethylhexyl citrate (ATEHC), triethylhexyl citrate (TEHC), acetyl triisononyl citrate (ATINC), triisononyl citrate (TINC) and the like. In addition, the trimellitate-based compound may also be diversely used in a similar form as the citrate-based compound, and examples thereof may include triisobutyl trimetllitate (TiBTM), trinormalbutyl trimetllitate (TnBTM), triethylhexyl trimetllitate (TEHTM), triisononyl trimetllitate (TINTM) and the like.

When using the citrate-based compound, the trimellitate-based compound or the epoxidized fatty acid alkyl ester compound as the additive, plasticizing efficiency may be enhanced, tensile strength or an elongation rate may be enhanced, or resistance for stress migration may increase depending on the added compounds. For example, depending on a molecular weight, materials having a low molecular weight are capable of improving effects such as plasticizing efficiency, and materials having a relatively large molecular weight are capable of improving tensile strength or a migration property.

The resin may use ethylene vinyl acetate, polyethylene, polyketone, polypropylene, polyvinyl chloride, polystyrene, polyurethane, thermoplastic elastomers, a mixture thereof or the like, and by adding the plasticizer composition, resin compositions effective in both compound formularization and/or sheet formularization may be provided.

The resin composition may further include a filler. The filler may be included in 0 parts by weight to 300 parts by weight, preferably in 50 parts by weight to 200 parts by weight and more preferably in 100 parts by weight to 200 parts by weight based on 100 parts by weight of the resin.

The filler may use fillers known in the art, and is not particularly limited. Examples thereof may include a mixture of one or more types selected from the group consisting of silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate and barium sulfate.

In addition, according to one embodiment of the present invention, the resin composition may further include other additives such as a stabilizer as necessary.

The other additives such as a stabilizer may be each included in, for example, 0 parts by weight to 20 parts by weight and preferably in 1 part by weight to 15 parts by weight based on 100 parts by weight of the resin.

Examples of the stabilizer that may be used according to one embodiment of the present invention may include a calcium-zinc-based (Ca—Zn-based) stabilizer such as a complex stearic acid salt of calcium—zinc, but are not limited thereto.

The resin composition may be used in various fields, and, as nonlimiting examples, may be used in manufacturing wires, flooring materials, automotive interior materials, films, sheets, wallpapers or tubes.

As means for preparing the plasticizer composition in the present invention, a blending method may be used, and one example of the blending preparation method is as follows.

An isophthalate-based material and a phthalate-based material are prepared.

The plasticizer composition may be prepared by blending the isophthalate-based material and the phthalate-based material in 99:1 to 1:99 as a weight ratio.

In the blending preparation method, the isophthalate-based material may be prepared using a direct esterification reaction through introducing isophthalic acid to an alcohol, then adding a catalyst, and reacting the result under nitrogen atmosphere; removing the unreacted alcohol, and neutralizing the unreacted acid; and dehydrating and filtering through vacuum distillation.

In addition, examples of the alcohol used in the blending preparation method may include isononyl alcohol, ethylhexyl alcohol and the like, and the alcohol may be used in a range of 150 mol % to 500 mol %, 200 mol % to 400 mol %, 200 mol % to 350 mol %, 250 mol % to 400 mol % or 270 mol % to 330 mol % based on 100 mol % of the isophthalic acid.

Moreover, the alcohol used in the blending preparation method may be used in a range of 150 mol % to 500 mol %, 200 mol % to 400 mol %, 200 mol % to 350 mol %, 250 mol % to 400 mol % or 270 mol % to 330 mol % based on 100 mol % of the isophthalic acid.

Meanwhile, the catalyst used in the blending preparation method is not particularly limited as long as it is capable of being used in an esterification reaction, and examples thereof may include one or more types selected from among acid catalysts such as sulfuric acid, hydrochloric acid, phosphoric acid, nitric acid, paratoluenesulfonic acid, methanesulfonic acid, ethanesulfonic acid, propanesulfonic acid, butanesulfonic acid and alkyl sulfuric acid, metal salts such as aluminum sulfate, lithium fluoride, potassium chloride, cesium chloride, calcium chloride, iron chloride and aluminum phosphate, metal oxides such as heteropolyacid, natural/synthetic zeolite, cation and anion exchange resins, and organic metals such as tetra alkyl titanate and polymers thereof. As specific examples thereof, tetra alkyl titanate may be used as the catalyst.

The amount of the catalyst used may be different depending on the types, and as one example, a homogeneous catalyst may be used in a range of 0.01% by weight to 5% by weight, 0.01% by weight to 3% by weight, 1% by weight to 5% by weight or 2% by weight to 4% by weight with respect to 100% by weight of the total reactants, and a heterogeneous catalyst may be used in a range of 5% by weight to 200% by weight, 5% by weight to 100% by weight, 20% by weight to 200% by weight or 20% by weight to 150% by weight with respect to the total weight of the reactants.

Herein, the reaction temperature may be in a range of 180° C. to 280° C., 200° C. to 250° C. or 210° C. to 230° C.

What is claimed is:

1. A resin composition comprising:
   100 parts by weight of a resin; and
   1 part by weight to 80 parts by weight of a plasticizer composition,
   wherein the plasticizer composition includes an isophthalate-based material and a phthalate-based material,
   wherein the isophthalate-based material and the phthalate-based material have a weight ratio of 99:1 to 1:99,
   wherein the isophthalate-based material includes diisononyl isophthalate (DINIP), diethylhexyl isophthalate (DEHIP) or a mixture thereof, and
   wherein the phthalate-based material includes di(2-propylheptyl)phthalate (DPHP), diisodecyl phthalate (DIDP) or a mixture thereof.

2. The resin composition of claim 1, wherein the isophthalate-based material and the phthalate-based material have a weight ratio of 99:1 to 10:90.

3. The resin composition of claim 1, wherein the isophthalate-based material and the phthalate-based material have a weight ratio of 99:1 to 30:70.

4. The resin composition of claim 3, wherein the isophthalate-based material and the phthalate-based material have a weight ratio of 99:1 to 70:30.

5. The resin composition of claim 1, wherein the plasticizer composition further includes an additive, and the additive is included in 1 part by weight to 100 parts by weight with respect to 100 parts by weight of a mixed weight of the isophthalate-based material and the phthalate-based material.

6. The resin composition of claim 5, wherein the additive includes any one selected from the group consisting of citrate-based compounds, trimellitate-based compounds and epoxidized fatty acid alkyl ester compounds.

7. The resin composition of claim 5, wherein the additive includes one or more types selected from the group consisting of epoxy fatty acid methyl ester (eFAME), acetyl tributyl citrate (ATBC), tributyl citrate (TBC), acetyl triethylhexyl citrate (ATEHC), triethylhexyl citrate (TEHC), acetyl triisononyl citrate (ATINC), triisononyl citrate (TINC), triisobutyl trimellitate (TiBTM), trinormalbutyl trimellitate (TnBTM), triethylhexyl trimellitate (TEHTM) and triisononyl trimellitate (TINTM).

8. The resin composition of claim 1, wherein the resin is one or more types selected from the group consisting of ethylene vinyl acetate, polyethylene, polyketone, polypropylene, polyvinyl chloride, polystyrene, polyurethane and thermoplastic elastomers.

9. The resin composition of claim 1, which is used in manufacturing one or more types selected from the group consisting of wires, flooring materials, automotive interior materials, films, sheets, wallpapers and tubes.

10. A method for preparing a resin composition comprising:
- preparing an isophthalate-based material and a phthalate-based material;
- obtaining a plasticizer composition by blending the isophthalate-based material and the phthalate-based material to have a weight ratio of 99:1 to 1:99; and
- mixing 100 parts by weight of a resin and 1 part by weight to 80 parts by weight of the plasticizer composition,
- wherein the isophthalate-based material includes diisononyl isophthalate (DINIP), diethylhexyl isophthalate (DEHIP) or a mixture thereof, and
- wherein the phthalate-based material includes di(2-propylheptyl)phthalate (DPHP), diisodecyl phthalate (DIDP) or a mixture thereof.

11. The method for preparing a resin composition of claim 10, further comprising:
- mixing an additive in 1, part by weight to 100 parts by weight with respect to 100 parts by weight of a mixed weight of the isophthalate-based material and the phthalate-based material after the obtaining of a plasticizer composition through blending.

12. The method for preparing a resin composition of claim 11, wherein the additive includes one or more compounds selected from the group consisting of citrate-based compounds, trimellitate-based compounds and epoxidized fatty acid alkyl ester compounds.

* * * * *